United States Patent [19]

Still

[11] 4,293,422

[45] Oct. 6, 1981

[54] FLASH CHROMATOGRAPHY

[76] Inventor: W. Clark Still, 560 Riverside Dr., New York, N.Y. 10027

[21] Appl. No.: 54,982

[22] Filed: Jul. 5, 1979

[51] Int. Cl.$^3$ .............................................. B01B 15/08
[52] U.S. Cl. ......................................... 210/656; 55/67
[58] Field of Search ................ 55/67; 210/198.2, 656, 210/659

[56] References Cited

PUBLICATIONS

Rapaid Chromatographic Technique for Preparative Separations with Modern Resolution by Still, Kahn and Mitra, a reprint from the Journal of Organic Chemistry, 43, 2923 (2978).

*Primary Examiner*—John Adee
*Attorney, Agent, or Firm*—Brooks, Haidt, Haffner & Delahunty

[57] ABSTRACT

A short vertical column is utilized to confine a short bed of adsorbent horizontally which has vertically defined upper and lower ends. Space in the column is provided to define a zone for horizontally defined liquid above and in contact with the bed. Liquid solvent is then placed in the column above bed to wet the bed, and positive gas pressure is applied to the liquid above the bed to drive entraped gases out of the bed. The solvent level is then lowered to the upper level of the bed. The sample is then added and gas pressure is used to drive the solvent and sample into the bed. The bed is eluted with fresh solvent in the same manner.

3 Claims, 1 Drawing Figure

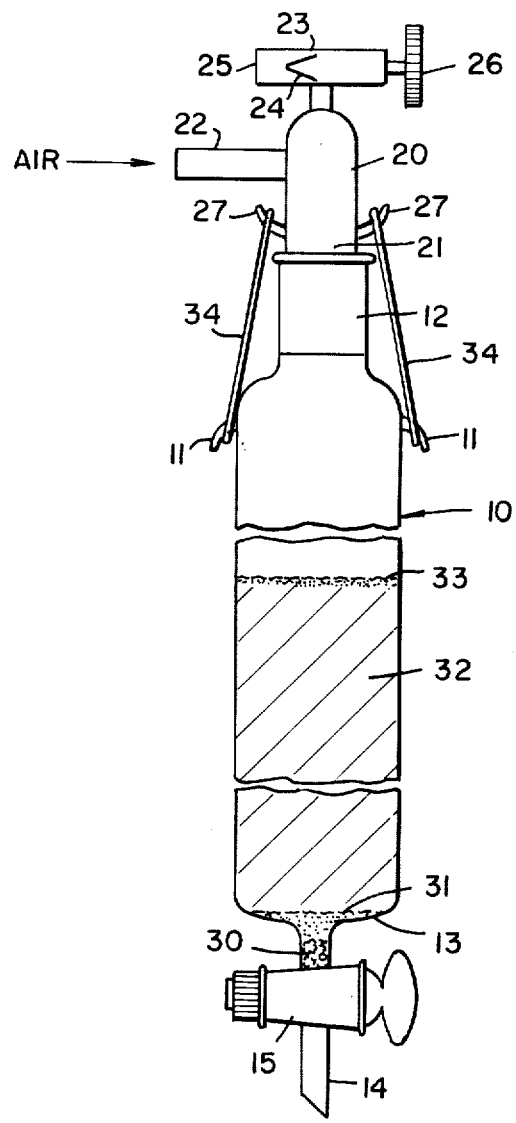

FLASH CHROMATOGRAPHY

This invention relates adsorption chromatography and in particular provides a liquid chromatographic method for high speed resolution of relatively large scale quantities of organic compounds.

Large scale preparative separations are traditionally carried out by tedious, long column chromatography. Although the results are sometimes satisfactory, the technique is always time consuming and frequently gives poor recovery due to band tailing. These problems are especially acute when samples of greater than one or two grams must be separated. Several preparative systems have evolved which reduce separation times to one to three hours and allow a resolution of components having $\Delta R_f \geq 0.05$ on analytical thin layer chromatography. These systems include medium pressure cromatography and short column cromatography.

It is a principal object of this invention to provide a substantially faster technique for routine purification of reaction products which is inexpensive to set up and operate and allow separations of samples weighing from 0.01-100. grams in ten to fifteen minutes.

These and other objects of this invention are basically achieved using a gas pressure driven hybrid of medium pressure and short column chromatography. In accordance with this invention a short vertical column is utilized to confine a short bed of adsorbent particles horizontally which has vertically defined upper and lower ends. Space in the column is provided to define a zone for horizontally confining liquid above and in contact with the bed. Liquid solvent is then placed in the column above the bed to wet the bed, and positive gas pressure, such as air pressure, is applied to the liquid above the bed to drive entrapped gases out of the bed. The solvent level is then lowered to the upper level of the bed. Thereafter solvent containing organic compounds to be resolved is placed in the column above the bed, and positive gas pressure is then applied to the solvent containing the compounds to drive the compounds into the bed. The solvent theretofore in the bed is displaced and withdrawn from beneath the bed. Thereafter, fresh solvent is placed in the column above the bed to serve as eluant, and positive gas pressure is again applied to the top of the column to drive the eluant into the bed at a rate in excess of 1.0 inches, preferably about 2.0 inches, per minute. The eluant is withdrawn from beneath the bed as it displaced and is separated into fractions as it is withdrawn.

The preferred adsorbent is silica gel. It has been found that particle size affects the resolution and that a particle size of 40-63 μm gives optimum results. Surprisingly the most popular grade (63-200 μm) gives the poorest resolution, and particle sizes less than 40 μm offer no improvement in resolution. Slurry packing, incremental dry packing and single portion dry packing give identical results with 40-63 μm gel, and hence, since the last is the simplest to use, it is the preferred technique for packing the adsorbent.

Column performance is quite sensitive to the rate of elution and is best with relatively high eluant flow rates. The gas pressure on the top of the column which is utilized to drive the eluant should be sufficient to obtain flow rates of eluant in excess of 1.0 inches per minute. One good solvent system is a mixture of ethyl acetate with petroleum ether. With this solvent system the optimum drop in the bed of the eluant is $2.0 \pm 0.1$ inches per minute. Resolution falls off drastically at rates in excess of 3 inches per minute.

The solvent system should be one which gives good separation and moves the desired component to $R_f$ from 0.25 to 0.5 on an analytical thin layer chromatograph. If this $R_f$ is given by a solvent having less than 2% of the polar component a slightly less polar eluant is desirable, thus if 1% ethyl acetate/petroleum ether gives a compound an $R_f$ of 0.35 on thin layer chromatograph, the column should be run with 0.5% ethyl acetate. If the sample is only partially soluble in the eluant, just enough more of the polar component should be added to give complete dissolution. Large quantities of very polar impurities are best removed prior to chromatography so that excessive quantities of solvent or large increases in solvent polarity will be unnecessary for sample application. Other examples of solvent systems which are often useful are acetone/petroleum ether or acetone/methylene chloride. Viscosities of solvent should be kept low, as the high viscosity solvents require slower optimum resolution flow rates.

The time required to elute the desired components from the column is generally so fast (5–10 minutes) that fraction collection is best done using a simple rack holding 40, 20×150 mm test tubes. Small fractions are typically collected early in the elution with larger ones being collected toward the end of the chromatography. Separated components are conveniently detected by spotting approximately 5 1 μL of each fraction along the long side of a thin layer chromatograph plate, and then by developing the plate sideways.

Generally, clean separation of compounds having $\Delta R_f \geq 0.15$ in less than 15 minutes and in many cases separations at $\Delta R_f \approx 0.10$ were possible.

The amount of sample used in a given column is proportional to its cross sectional area. The following table is illustrative of the relationship between column diameter and sample volume.

| column diameter, mm | vol of eluant mL | sample typical loading (mg) | | typical fraction size mL |
|---|---|---|---|---|
| | | $\Delta R_f \geq 0.2$ | $\Delta R_f \geq 0.1$ | |
| 10 | 100 | 100 | 40 | 5 |
| 20 | 200 | 400 | 160 | 10 |
| 30 | 400 | 900 | 360 | 20 |
| 40 | 600 | 1600 | 600 | 30 |
| 50 | 1000 | 2500 | 1000 | 50 |

The above is based upon a bed depth of adsorbent of 5.5 to 6 inches.

For a more complete understanding of the practical application of the principles of this invention, reference is made to the appended drawings which illustrate an apparatus suitable for carrying out the method of this invention.

In the drawings, the reference numeral 10 designates a cylindrical glass column having a pair of ears 11 at its upper end and which is provided with a neck fitting 12 at its upper end. Column 10 has a flattened bottom 13 and a depending glass leg 14 which is provided with a stop cock 15 for withdrawing liquids from the column 10. Column 10 has an interior space approximately 18 inches high and can be of any diameter from 10 to 50 mm, depending on the size of sample to be resolved.

Column 10 is connected to a source of compressed air by an air controller 20 in the form of a tube having an open lower end sized to be received snugly in neck fitting 12. Controller 20 has a lateral port and fitting 22 for connection to the source of compressed air and is closed at its upper end, except that it is provided with a needle valve 23 for bleeding air from the interior of controller 20 past a controllable needle 24 through a bleed port 25. Needle valve 23 is also provided with a knurled nut 26 which can be rotated to set the position of needle 24 and thus control the bleed of air from the interior of controller 20. Controller 20 is also provided with a pair of ears 27.

A small plug 30 of glass wool is placed in column 10 at the connection of outlet 14 to bottom 13. Placement of plug 30 is facilitated by the use of two telescoping lengths of glass tubing having 6 and 8 mm OD. Thereafter, a smooth layer 31 of 50–100 mesh sand having a thickness of approximately ⅛ inch is added to cover the bottom of the column. Dry 40–63 μm silica gel 32 is then poured into the column in a single portion to a depth of approximately 5.5 to 6 inches. The preferred silica gel is silica gel 60, No. 9385, a proprietary product manufactured by E. Merck.

With stop cock 15 open column 10 is gently tapped vertically on the bench top to pack layer 32 of the gel. Thereafter, a second ⅛ inch layer 33 of sand is carefully placed on the flat top of dry gel bed 32, and column 10 is clamped for pressure packing and elution.

The solvent chosen for the particular separation is then carefully poured over sand layer 33 to fill column 10 completely. Flow controller 20 is placed in position and clamped with a pair of rubber bands 34 which fit over ears 11 and 27. With needle valve 23 fully open fitting 22 is connected to the compressed air supply which should have a valve for controlling the air flow to controller 20. This main air valve should be opened only slightly and a finger is placed fairly tightly over bleed port 25. This causes the pressure above bed 32 to climb rapidly and compress the silica gel as solvent is forced through bed 32. It is important to maintain the pressure until all the air in bed 32 is expelled and the lower part of column 10 is cool. If this is not done, bed 32 will fragment and require repacking (unless the separation desired is a trivial one). Particular care is necessary with large diameter columns.

Air pressure is then released by partially unblocking the bleed port 25, and excess eluant is forced out of column 10 above adsorbent bed 32. The top of the silica gel bed 32 should not be allowed to run dry, however.

With controller 20 removed, the sample to be resolved is applied by pipette as a 20–25% solution in the eluant solvent to the top of adsorbent bed 32. Flow controller 20 is briefly placed on top of column 10 to push all the sample into silica gel 32. Controller 20 is then removed, and the solvent used to pack the column, or fresh solvent, is then reused to elute column 10.

The walls of column 10 are washed down with a few ml of eluant. These washings are then pushed into bed 32 by replacing controller 20, and then with controller 20 removed column 10 is carefully filled with eluant so as not to disturb absorbent bed 32. Flow controller 20 is then resecured on column 10, and pressure is adjusted to cause the surface of the solvent in the column to fall 2.0 inches per minute. Fractions are collected until all the solvent has been used. Care should be taken, however, not to let column 10 run dry, since further elution is occasionally necessary. Approximately 5 μL of each fraction are spotted along the long side of a 7 cm by 2.5 cm thin layer chromatograph plate to identify those fractions containing the resolved compounds.

I claim:

1. A method of adsorption chromatography for separation of organic compounds in liquid solvent therefor, which includes:
   a. establishing an horizontally confined, vertically defined bed of adsorbent particles having a horizontally confined zone thereabove,
   b. placing said liquid solvent in said zone above said bed,
   c. applying positive gas pressure to said solvent above said bed to wet said bed whereby and until gases entrapped in said bed are driven out of said bed,
   d. lowering the level of solvent to the upper level of said bed,
   e. placing said solvent containing said compounds in said zone above said bed,
   f. applying positive gas pressure to said solvent containing said compounds above said bed to drive said solvent and compounds into said bed while withdrawing solvent displaced from said bed from beneath said bed,
   g. placing solvent (eluant) in said zone above said bed,
   h. applying positive gas pressure to said eluant above said bed to drive said eluant into said bed at a rate in excess of 1.0 inches per minute, and
   i. withdrawing from beneath said bed and separating into fractions eluant containing said compounds displaced from said bed.

2. A method according to claim 1 in which said adsorbent is silica gel having a particle size of 40–63 μm.

3. A method according to claim 1 in which said eluant is driven at a rate of 2 inches per minute.

* * * * *